United States Patent
Smith

(10) Patent No.: US 8,116,846 B2
(45) Date of Patent: *Feb. 14, 2012

(54) INTRAVASCULAR ANTENNA

(75) Inventor: Scott R. Smith, Chaska, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 223 days.

This patent is subject to a terminal disclaimer.

(21) Appl. No.: 12/181,948

(22) Filed: Jul. 29, 2008

(65) Prior Publication Data

US 2008/0294042 A1 Nov. 27, 2008

Related U.S. Application Data

(63) Continuation of application No. 10/840,549, filed on May 6, 2004, now Pat. No. 7,496,397.

(51) Int. Cl.
*A61B 5/055* (2006.01)

(52) U.S. Cl. ..................................... 600/423

(58) Field of Classification Search .................. 600/407, 600/423, 433, 435; 606/27; 128/898
See application file for complete search history.

(56) References Cited

U.S. PATENT DOCUMENTS

| | | |
|---|---|---|
| 3,326,207 A | 6/1967 | Egan |
| 4,304,239 A | 12/1981 | Perlin |
| 4,740,752 A | 4/1988 | Arakawa et al. |
| 4,899,757 A | 2/1990 | Pope, Jr. et al. |
| 4,960,106 A | 10/1990 | Kubakawa |
| 5,006,119 A | 4/1991 | Acker et al. |
| 5,050,607 A | 9/1991 | Bradley et al. |
| 5,057,106 A | 10/1991 | Kasevich et al. |
| 5,109,859 A | 5/1992 | Jenkins |
| 5,243,988 A | 9/1993 | Sieben et al. |
| 5,269,319 A | 12/1993 | Schulte et al. |
| 5,275,597 A | 1/1994 | Higgins et al. |
| 5,307,814 A | 5/1994 | Kressel et al. |
| 5,318,025 A | 6/1994 | Dumoulin et al. |
| 5,354,324 A | 10/1994 | Gregory |
| 5,364,392 A | 11/1994 | Warner et al. |
| 5,405,346 A | 4/1995 | Grundy et al. |
| 5,438,997 A | 8/1995 | Sieben |
| 5,470,352 A | 11/1995 | Rappaport |
| 5,476,095 A | 12/1995 | Schnall et al. |
| 5,513,637 A | 5/1996 | Twiss et al. |
| 5,543,712 A | 8/1996 | Arakawa et al. |
| 5,676,151 A | 10/1997 | Yock |

(Continued)

FOREIGN PATENT DOCUMENTS

EP 0385367 9/1990

(Continued)

OTHER PUBLICATIONS

JP Office Action dated Jan. 11, 2011 (with partial English translation) from JP Application No. 2007-511687, 6 pages.

(Continued)

*Primary Examiner* — Michael Rozanski

(74) *Attorney, Agent, or Firm* — Fish & Richardson P.C.

(57) ABSTRACT

The present invention relates to an elongate intravascular device adapted to be advanced through a vessel of a subject. The present invention further includes an antenna which is disposed on an inflatable member such that the antenna can be increased or decreased in size to more accurately tune the system in which it is employed.

12 Claims, 3 Drawing Sheets

U.S. PATENT DOCUMENTS

| | | | |
|---|---|---|---|
| 5,693,082 A | 12/1997 | Warner et al. | |
| 5,713,363 A | 2/1998 | Seward et al. | |
| 5,713,854 A | 2/1998 | Inderbitzen et al. | |
| 5,722,410 A | 3/1998 | NessAiver | |
| 5,728,079 A | 3/1998 | Weber et al. | |
| 5,776,176 A | 7/1998 | Rudie | |
| 5,792,055 A | 8/1998 | McKinnon | |
| 5,807,330 A | 9/1998 | Teitelbaum | |
| 5,819,737 A | 10/1998 | Young et al. | |
| 5,840,031 A | 11/1998 | Crowley | |
| 5,868,674 A | 2/1999 | Glowinski et al. | |
| 5,920,294 A * | 7/1999 | Allen | 343/912 |
| 5,928,145 A | 7/1999 | Ocali et al. | |
| 5,931,819 A | 8/1999 | Fariabi | |
| 6,097,985 A | 8/2000 | Kasevich et al. | |
| 6,106,486 A | 8/2000 | Tenerz et al. | |
| 6,159,225 A | 12/2000 | Makower | |
| 6,165,127 A | 12/2000 | Crowley | |
| 6,165,166 A | 12/2000 | Samuelson et al. | |
| 6,235,054 B1 | 5/2001 | Berg et al. | |
| 6,253,769 B1 | 7/2001 | LaFontaine et al. | |
| 6,263,229 B1 | 7/2001 | Atalar et al. | |
| 6,284,971 B1 | 9/2001 | Atalar et al. | |
| 6,304,769 B1 | 10/2001 | Arenson et al. | |
| 6,458,098 B1 | 10/2002 | Kanesaka | |
| 6,560,475 B1 | 5/2003 | Viswanathan | |
| 6,592,526 B1 | 7/2003 | Lenker | |
| 6,593,884 B1 | 7/2003 | Gilboa et al. | |
| 6,606,513 B2 | 8/2003 | Lardo et al. | |
| 6,628,980 B2 | 9/2003 | Atalar et al. | |
| 6,635,054 B2 | 10/2003 | Fjield et al. | |
| 6,675,033 B1 | 1/2004 | Lardo et al. | |
| 6,699,241 B2 | 3/2004 | Rappaport et al. | |
| 6,729,336 B2 | 5/2004 | Da Silva et al. | |
| 7,194,297 B2 | 3/2007 | Talpade et al. | |
| 2002/0045816 A1 | 4/2002 | Atalar et al. | |
| 2003/0016186 A1 | 1/2003 | Watanabe et al. | |
| 2003/0097064 A1 | 5/2003 | Talpade et al. | |
| 2003/0120207 A1 | 6/2003 | Wang | |
| 2005/0228370 A1 * | 10/2005 | Sterzer et al. | 606/33 |
| 2005/0251031 A1 | 11/2005 | Smith | |
| 2005/0251032 A1 | 11/2005 | Smith | |
| 2008/0021315 A1 | 1/2008 | Smith | |
| 2008/0208043 A1 | 8/2008 | Smith et al. | |

FOREIGN PATENT DOCUMENTS

| | | |
|---|---|---|
| EP | 0977308 | 2/2000 |
| JP | 5327138 | 12/1993 |
| JP | 2575400 | 1/1997 |
| JP | 2655940 | 9/1997 |
| JP | 11041027 | 2/1999 |
| JP | 2000-116615 | 4/2000 |
| JP | 2001-523407 | 11/2001 |
| NL | 1004381 | 5/1998 |
| WO | WO 94/12102 | 6/1994 |
| WO | WO 9729684 | 8/1997 |
| WO | WO 99/37211 | 7/1999 |
| WO | WO 99/40396 | 8/1999 |
| WO | WO 00/33734 | 6/2000 |
| WO | WO 00/64003 | 10/2000 |
| WO | 03/041591 | 5/2003 |
| WO | 2005/107841 | 11/2005 |
| WO | 2005/109025 | 11/2005 |

OTHER PUBLICATIONS

EP Communication from EP Application No. 05741950.9 mailed Apr. 8, 2010, 7 pages.

International Search Report and Written Opinion from International Application No. PCT/US2005/015462 mailed Aug. 26, 2005, 17 pages.

International Search Report and Written Opinion from PCT/US2005/016098 mailed Oct. 20, 2005, 12 pages.

* cited by examiner

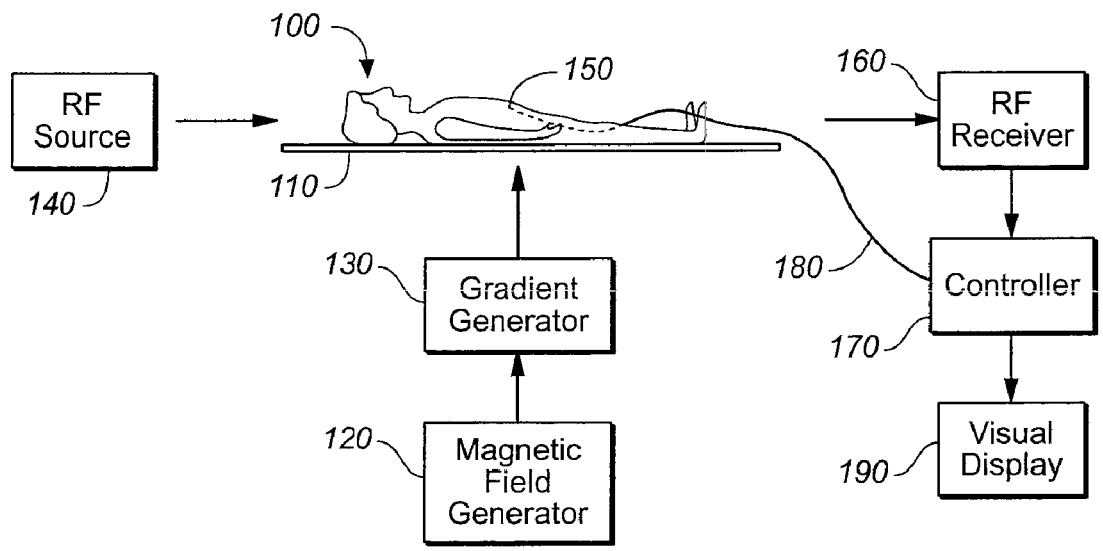
FIG._1
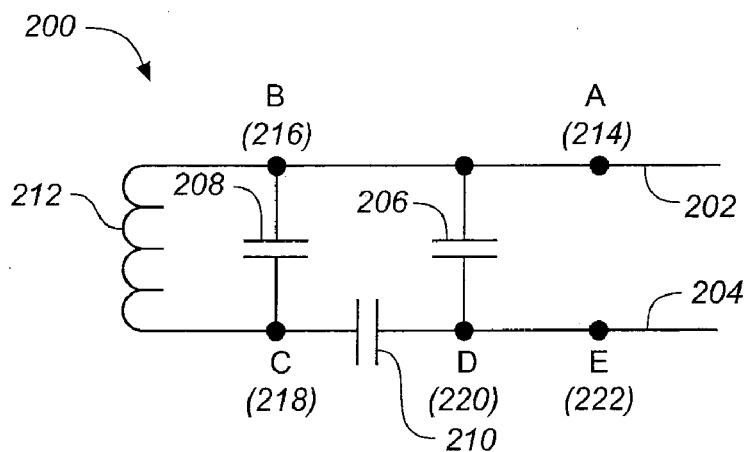
FIG._2 (PRIOR ART)

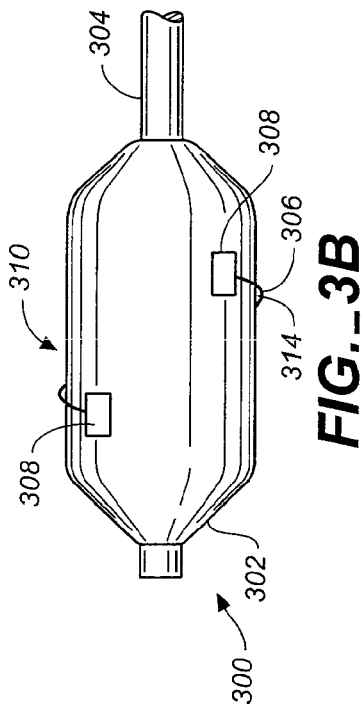
FIG._3B
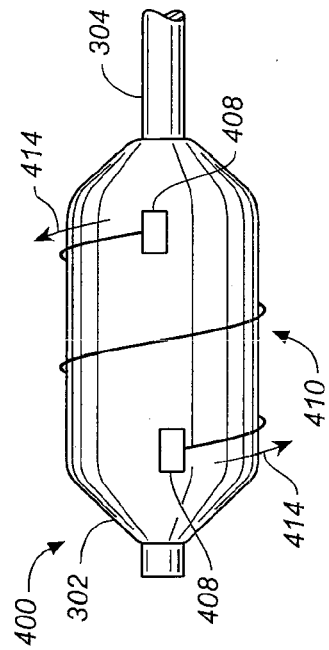
FIG._4B
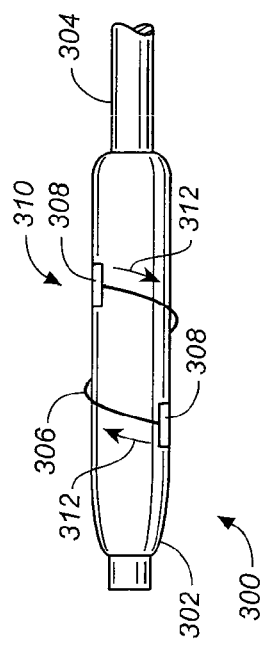
FIG._3A
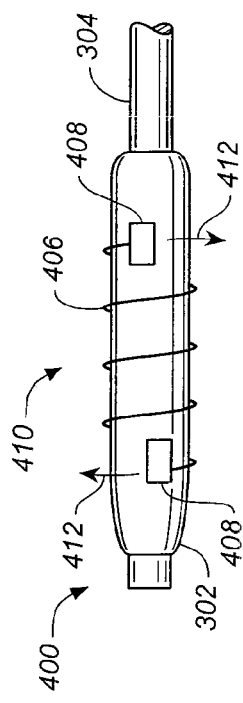
FIG._4A
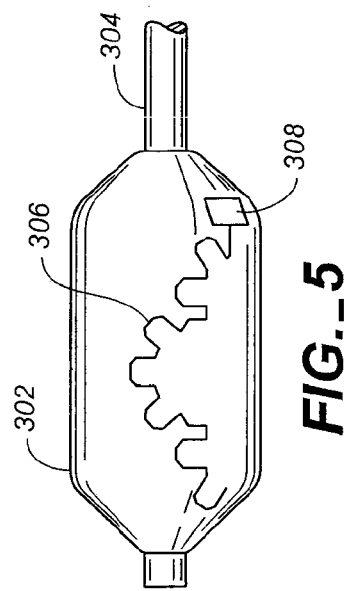
FIG._5

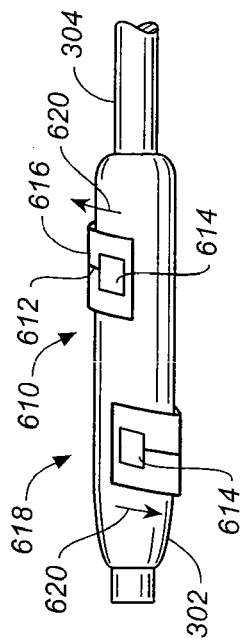
FIG._6A
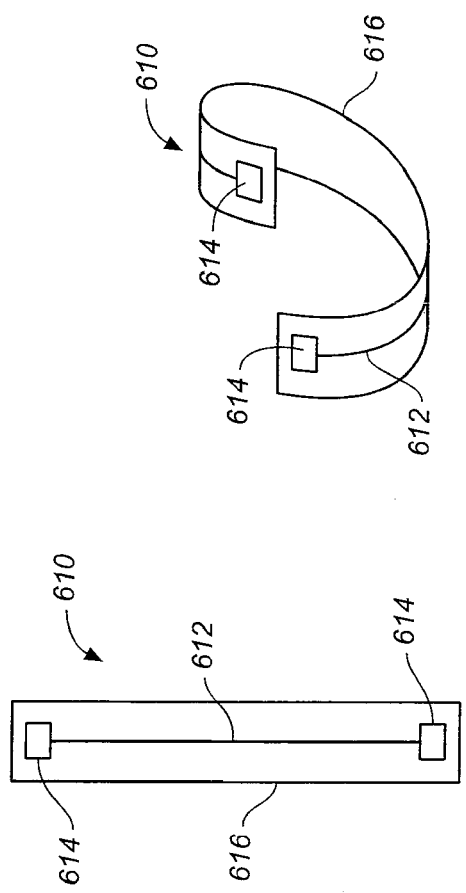
FIG._6B
FIG._6C
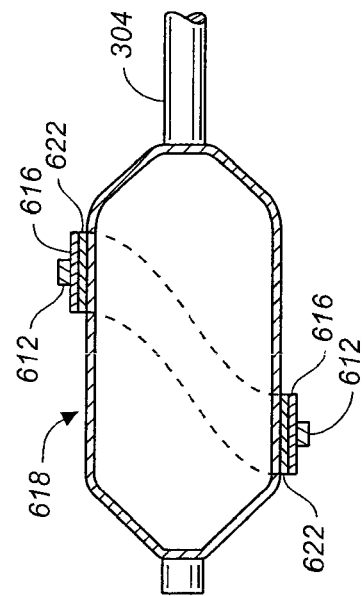
FIG._6E
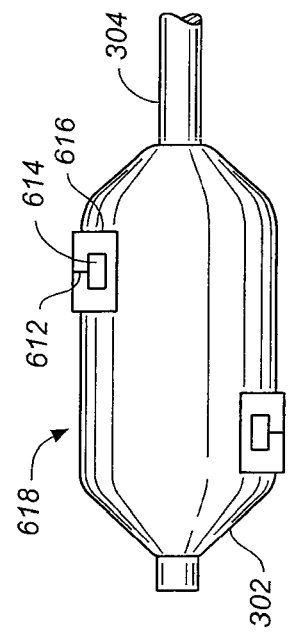
FIG._6D

INTRAVASCULAR ANTENNA

CROSS-REFERENCE TO RELATED APPLICATIONS

This application is a continuation of, and claims priority to, U.S. application Ser. No. 10/840,549, filed on May 6, 2004, which is issued as U.S. Pat. No. 7,496,397 on Feb. 24, 2009, entitled INTRAVASCULAR ANTENNA, the entire contents of which are incorporated herein by reference.

The present application hereby makes reference to U.S. patent application Ser. No. 10/008,380, filed Nov. 13, 2001, entitled IMPEDANCE-MATCHING APPARATUS AND CONSTRUCTION FOR INTRAVASCULAR DEVICE, which is issued as U.S. Pat. No. 7,194,297 on Mar. 20, 2007. The present application also makes reference to pending U.S. patent application Ser. No. 11/954,861, filed Dec. 12, 2007, entitled APPARATUS AND CONSTRUCTION FOR INTRAVASCULAR DEVICE.

BACKGROUND

The present invention relates generally to intravascular devices. More particularly, the present invention relates to antennae used in intravascular magnetic resonance imaging (MRI) devices. Intravascular imaging involves generating an image of tissue surrounding an intravascular device. Visualization involves generating an image of a catheter or other intravascular device on another image, or by itself, usually through localized signals from tissue immediately adjacent the device.

Imaging, visualization and tracking of catheters and other devices positioned within a body may be achieved by means of a magnetic resonance imaging (MRI) system. Typically, such a magnetic resonance imaging system may be comprised of a magnet, a pulsed magnetic field gradient generator, a transmitter for electromagnetic waves in radio frequency (RF), a radio frequency receiver, and a controller. In a common implementation, an antenna is disposed either on the device to be tracked or on a guidewire or catheter (commonly referred to as an MR catheter) used to assist in the delivery of the device to its destination. In one known implementation, the antenna comprises an electrically conductive coil that is coupled to a pair of elongated electrical conductors that are electrically insulated from each other and that together comprise a transmission line adapted to transmit the detected signal to the RF receiver.

In one embodiment, the coil is arranged in a solenoid configuration. The patient is placed into or proximate the magnet and the device is inserted into the patient. The magnetic resonance imaging system generates electromagnetic waves in radio frequency and magnetic field gradient pulses that are transmitted into the patient and that induce a resonant response signal from selected nuclear spins within the patient. This response signal induces current in the coil of electrically conductive wire attached to the device. The coil thus detects the nuclear spins in the vicinity of the coil. The transmission line transmits the detected response signal to the radio frequency receiver, which processes it and then stores it with the controller. This is repeated in three orthogonal directions. The gradients cause the frequency of the detected signal to be directly proportional to the position of the radio-frequency coil along each applied gradient.

The position of the radio frequency coil inside the patient may therefore be calculated by processing the data using Fourier transformations so that a positional picture of the coil is achieved. In one implementation this positional picture is superposed with a magnetic resonance image of the region of interest. This picture of the region may be taken and stored at the same time as the positional picture or at any earlier time.

In a coil-type antenna such as that described above, it is desirable that the impedance of the antenna coil substantially match the impedance of the transmission line. In traditional impedance matching of MRI coils, shunt-series or series shunt capacitor combinations suffice to tune the coil. In such traditional applications, the capacitors almost never pose a size constraint.

However, for intravascular coils, miniaturization of the tuning capacitors is necessary. Discrete components have been employed to construct matching and tuning circuits on intravascular devices. But such components are bulky and are not easily incorporated into the design of the device. Also, placement of the tuning capacitors away from the coil without a reduction in the signal-to-noise ratio (SNR) is desirable. It has been proposed to use open circuit stub transmission lines as a means of fabricating arbitrary or trimmable capacitors and to use short-circuited stubs as tuning inductors. Such probes are tuned by trimming the length of the coaxial cables. However, these circuits still result in a relatively large device that is not ideal for intravascular navigation. Also, the circuits require many connections and the fabrication process is relatively complex.

Another problem that arises with intravascular MRI antenna devices is that present day devices have a number of limitations. Such antennas include single loops, and saddle coils. Those antennas are resonant at some frequency, but that frequency is typically in the gigahertz range which is quite high. The antennae are typically small compared to the wavelength of the signal to be detected. Therefore, it is very difficult to tune a conventional coil antenna to optimize for that wavelength. In prior systems, the circuit was tuned using the discrete inductors and capacitors on the coil antenna mentioned above.

It can thus be seen that, often, it is desirable to make the antenna as large as possible. However, the diameter of the antenna is limited by the need to access the vessel. Simple expanding loops partially address this limitation, but they can be difficult to deploy in the vessel.

The present invention addresses at least one, and possibly more, of these, problems and offers advantages over the prior art.

SUMMARY

The present invention relates to an elongated intravascular device adapted to be advanced through a vessel of a body. The present invention further includes an antenna which is disposed on an inflatable member such that the antenna can be increased or decreased in size to more accurately tune the systems in which it is employed.

DESCRIPTION OF DRAWINGS

FIG. 1 is a partial block diagram of an illustrative magnetic resonance imaging and intravascular guidance system in which embodiments of the present invention can be employed.

FIG. 2 is a schematic diagram of an impedance-matching circuit that is known in the art.

FIGS. 3A and 3B illustrate an antenna disposed on an inflatable member in the contracted and expanded or deployed positions, respectively.

FIGS. 4A and 4B illustrate another type of antenna on an inflatable member in the retracted and expanded or deployed positions, respectively.

FIG. 5 illustrates yet another type of antenna disposed on an inflatable member.

FIGS. 6A and 6B illustrate-one embodiment of an antenna printed on a flex circuit.

FIGS. 6C and 6D illustrate the flex circuit shown in FIGS. 6A and 6B disposed on an inflatable member in the retracted and deployed positions, respectively.

FIG. 6E is a cross sectional view of the flex circuit and inflatable member shown in FIG. 6D.

DETAILED DESCRIPTION

FIG. 1 is a partial block diagram of an illustrative magnetic resonance imaging, visualization and intravascular guidance system in which embodiments of the present invention could be employed. In FIG. 1, subject 100 on support table 110 is placed in a homogeneous magnetic field generated by magnetic field generator 120. Magnetic field generator 120 typically comprises a cylindrical magnet adapted to receive subject 100. Magnetic field gradient generator 130 creates magnetic field gradients of predetermined strength in three mutually orthogonal directions at predetermined times. Magnetic field gradient generator 130 is illustratively comprised of a set of cylindrical coils concentrically positioned within magnetic field generator 120. A region of subject 100 into which a device 150, shown as a catheter, is inserted, is located in the approximate center of the bore of magnet 120.

RF source 140 radiates pulsed radio frequency energy into subject 100 and the MR active sample within device 150 at predetermined times and with sufficient power at a predetermined frequency to nutate nuclear magnetic spins in a fashion well known to those skilled in the art. The nutation of the spins causes them to resonate at the Larmor frequency. The Larmor frequency for each spin is directly proportional to the strength of the magnetic field experienced by the spin. This field strength is the sum of the static magnetic field generated by magnetic field generator 120 and the local field generated by magnetic field gradient generator 130. In an illustrative embodiment, RF source 140 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils such as surface coils may alternatively be used.

Device 150 is inserted into subject 100 by an operator. Device 150 may be a guide wire, a catheter, an ablation device or a similar recanalization device. Device 150 includes an RF antenna which detects MR signals generated in both the subject and the device 150 itself in response to the radio frequency field created by RF source 140. Since the internal device antenna is small, the region of sensitivity is also small. Consequently, the detected signals have Larmor frequencies which arise only from the strength of the magnetic field in the proximate vicinity of the antenna. The signals detected by the device antenna are sent to imaging, visualization and tracking controller unit 170 via conductor 180.

In an illustrative embodiment, external RF receiver 160 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils, such as surface coils, may alternatively be used. External RF receiver 160 can share some or all of its structure with RF source 140 or can have a structure entirely independent of RF source 140. The region of sensitivity of RF receiver 160 is larger than that of the device antenna and can encompass the entire subject 100 or a specific region of subject 100. However, the resolution which can be obtained from external RF receiver 160 is less than that which can be achieved with the device antenna.

The RF signals detected by external RF receiver 160 are sent to imaging, visualization and tracking controller unit 170 where they are analyzed together with the RF signals detected by the device antenna. A number of embodiments which are employed to address the difficulties in making connections to the antenna and to address fabrication process complexity are described in pending U.S. application Ser. No. 11/954,861 entitled APPARATUS AND CONSTRUCTION FOR INTRAVASCULAR DEVICE, filed on Dec. 12, 2007. That application also discusses a number of embodiments showing alternating layers of conductors and dielectric materials to construct components and circuits that can be used to tune a circuit that includes the intravascular device or to match impedances among components or segments of such a circuit.

To address the above-described problem, an illustrative embodiment set out in detail in the co-pending referenced application employs alternating layers of conductors and dielectric materials to construct components and circuits that can be used to tune a circuit of the intravascular device or to match impedances among components or segments of such a circuit. FIG. 2 is a schematic diagram of an impedance-matching circuit 200 that is known in the art. Impedance-matching circuit 200 includes transmission lines 202, 204, capacitances 206, 208, 210, and inductive coil 212. This circuit, with nodes 214, 216, 218, 220 and 222 is used in impedance matching.

Another problem associated with intravascular devices for use in the system shown in FIG. 1 arises with respect to employing a suitable antenna within the patient. FIG. 3A is a side view of an intravascular device 300 in accordance with one illustrative embodiment of the present invention. Intravascular device 300 illustratively includes an inflatable portion 302 supported by an elongate member (such as a catheter or guidewire) 304. In the embodiment shown in FIG. 3A, a conductor 306, with associated connection pads 308 are disposed on the inflatable member 302 to collectively form antenna portion 310.

In one illustrative embodiment, intravascular device 300, along with antenna 310, functions as an antenna in a system such as that shown in FIG. 1, to receive RF signals and transmit the signals back to a receiver/controller. In an alternative embodiment, intravascular device 300 performs functions in addition to acting as an antenna. For example, in one embodiment, device 300 can also serve as a guidewire used to assist in the delivery of another intravascular device to an intravascular location. In yet another embodiment, device 300 can serve as an ablation device used to disintegrate an occlusion in a vessel. In still another embodiment, device 300 is deployed as a dilatation device or other device supported by a catheter, and device 300 can be formed integrally with catheter 304 or separately therefrom.

FIG. 3A shows device 300 in its radially collapsed or retracted, delivery position and FIG. 3B shows device 300 in a radially expanded, or deployed position. In FIG. 3A, inflatable member 302 is deflated, and can be twisted or folded over on itself. When inflatable member 302 is inflated to the position shown in FIG. 3B, conductor 306 expands in the direction indicated by arrows 312 and conductor 306 forms a single turn antenna on the surface of inflatable member 302.

When expandable member 302 is deflated, antenna 310 moves in a direction opposite arrows 312 and thus acts to recoil to the position shown in FIG. 3A, either by folding or slightly twisting the material forming expandable member 302.

Connection pads 308 can be coupled to one or more conductors forming a transmission line extending proximally to the system shown in FIG. 1, across the dielectric balloon material. This can act as a variable tuning capacitor in the circuit since the capacitance may change as the balloon pressure is changed.

In one illustrative embodiment, inflatable member 302 is formed of a non-compliant material, such as polyethylene terephthalate (PET). This tends to avoid sheer failure at an interface between conductor 306 and connection pads 308 and the material forming inflatable member 302.

Conductor 306 and pads 308 can be printed on the surface of inflatable member 302 using any number of a variety of techniques. For example, lithography or transfer printing can create the patterns. For the conductive portions of antenna 310, gold may be one illustrative conductor for the circuits. In addition to gold, other materials can be used for the conductive portions of antenna 310 as well. For example, conductive polymers (polymers loaded with conductive particles) or other materials can used as well.

Inflation and flexing of inflatable member 302 can create additional stresses on the interface between inflatable member 302 and antenna 310. In addition, folding of inflatable member 302 can create sheer stress between the balloon and the conductors, and can also create tensile stresses in the conductors themselves. Thus, in one illustrative embodiment, the conductors 306 and 308 are not disposed over folding portions of inflatable member 302. In another embodiment, a tie layer 314 is used between the conductive portions of antenna 310 and the surface of inflatable member 302. The tie layer exhibits flexible, elastic characteristics that minimize sheer stress at the interface between the two materials. The tie layer can be any suitable form of material or coating that exhibits desired elastic behavior to reduce stresses seen at the interface between antenna 310 and expandable member 302 to a desirable level. In another embodiment, areas of the antenna are configured (such as with increased flexibility) to be more easily folded or bent without fatiguing and without exhibiting unduly increased stress.

FIGS. 4A and 4B show another device 400 which is similar to device 300 shown in FIGS. 3A and 3B, except that the antenna 410 forms a multiple turn antenna, rather than a single turn antenna. When inflatable member 302 is deflated, connection pads 408 move in the directions indicated by arrows 412 thus causing antenna 410 to coil about inflatable member 302 by folding inflatable member 302, or by slightly twisting it. However, when inflatable member 302 is expanded to the position shown in FIG. 4B, connection pads 408 move in the direction indicated by arrows 414 to cause the diameters of the turns in the antenna 410 to increase.

FIG. 5 illustrates yet another type of antenna which can be disposed on the surface of inflatable member 302. FIG. 5 is similar to the embodiments shown in FIGS. 3A-4B, and some items are similarly numbered. However, the antenna disposed on inflatable member 302 in FIG. 5 is a fractal antenna. As used herein, a fractal antenna is an antenna which takes one of two main geometric types (deterministic, and random, or chaotic). Random fractals may appear as random walks, dendrites, or similar to lightning bolts. Deterministic fractals apply a generator on successive size scales. For purpose of the present discussion, deterministic fractals are deemed to have a finite number of (and at least 2) self-similar iterations.

Fractal antennas can be formed much smaller than conventional antennas, with the same performance results. Similarly, fractal antennas are "self-loading" so fewer coils and capacitors are required to make them resonant. Some fractal antennas are available from Fractal Antenna Systems, Inc. of Maiden, Mass.

Thus, FIG. 5 illustrates a device 500, similar to devices 300 and 400, except that it employs a fractal antenna 502. Of course, the fractal antenna 502 can be deterministic or random, with any suitable number of iterations, as desired. Thus, one embodiment of the invention utilizes a "complex" antenna shape that is more geometrically complex than simple loop or saddle loop antenna configurations. For instance, these complex shapes have more geometric features (e.g., angles, shapes or properties) than a simple loop or saddle loop and may illustratively be put on the inflatable member using a technique, or in a configuration, that facilitates folding or collapsing of the inflatable member without breaking or rendering electrically discontinuous, the antenna. This can be done, for example, by printing the complex antenna shape on the inflatable member, by using a tie layer (described below), by making fold regions in the antenna shape that are of increased resilience or otherwise less susceptible to damage from folding or collapsing the inflatable member, or simply by positioning the complex antenna shape on the inflatable member so it need not be folded.

FIGS. 6A-6E illustrate another embodiment of the present invention. FIG. 6A shows that in one illustrative embodiment, an antenna 610, which includes a conductive portion 612 and connection pads 614, is disposed on a flexible circuit material 616. In one illustrative embodiment, antenna 610 is printed on flex circuit substrate 616 which is formed from a suitable material, such as polyimide.

In one illustrative embodiment, substrate 616 and antenna 610 are biased into a wrapped conformation (or scrolled shape) such as that shown in FIG. 6B. Flex circuit substrate 616, with antenna 610 disposed thereon, is then placed on an inflatable member 618, as shown in FIG. 6C. FIG. 6C shows that inflatable member 618 is similar to inflatable member 302, and can be supported by a catheter 304. FIG. 6C also shows that inflatable member 618 is in the collapsed or uninflated position.

In one illustrative embodiment, flex circuit substrate 616 is attached only at one place (e.g., an end adjacent pad 614 or at an intermediate point) to the surface of inflatable member 618. Thus, as inflatable member 618 is inflated to the position shown in FIG. 6D, the attached, portion of substrate 616 remains fixed to the surface of inflatable member 616 while the remainder is allowed to move or slide relative to the surface of inflatable member 618.

This effectively causes the ends of substrate 616 to move relative to one another in the direction indicated by arrow 620 in FIG. 6C to the position shown in FIG. 6D. Of course, this causes antenna 610 (which is shown as a single loop antenna but could be formed as any other antenna as well) to increase in its deployed diameter.

FIG. 6E shows a cross section of one embodiment of the device illustrated in FIGS. 6A-6D. FIG. 6E shows conductor 612 disposed on substrate 616 which is, itself, attached to the surface of inflatable member 618. The flex circuit substrate 616 can be attached using an adhesive, directly onto the surface of inflatable member 618 or it can be attached to a tie layer 622 disposed at the interface of inflatable member 618 and substrate 616. The flex circuits are commercially available and generally known. The tie layer may illustratively be any desirable tie layer, such as polyvinyl acetate, low durometer nylon, or polyester, etc. Other tie layers can be used as well.

It can thus be seen that the present invention provides unique devices for use in antennas in MRI systems. Such devices provide significant advantages over prior devices. The antenna in accordance with the present invention can take substantially any form such as a monopole, dipole, solenoid, fractal, etc. The present invention is contemplated to cover all antenna configurations.

Although the present invention has been described with reference to preferred embodiments, workers skilled in the art will recognize that changes may be made in form and detail without departing from the spirit and scope of the invention.

What is claimed is:

1. A device for insertion into a subject, comprising:
an elongate member having a distal portion and a proximal portion;
an inflatable member coupled to the distal portion of the elongate member;
an antenna comprising connection pads and one or more conductors, the connection pads coupled to the one or more conductors to form a transmission line in an impedance matching circuit, the antenna coupled to the inflatable member, where inflation of the inflatable member changes a dimension of the antenna and a capacitance in the impedance matching circuit;
a tie layer disposed at an interface between the inflatable member and the antenna, where the tie layer exhibits flexible and elastic characteristics that minimize sheer stress at the interface between the inflatable member and the antenna, wherein the tie layer is layered between the inflatable member and the antenna and a first surface of the tie layer is coupled to the inflatable member and a second surface that opposes the first surface is coupled to the antenna.

2. The device of claim 1, wherein the tie layer comprises at least one of polyvinyl, acetate, nylon or polyester.

3. The device of claim 1, wherein the antenna is biased into a wrapped conformation.

4. The device of claim 1, wherein the one or more conductors form a single turn antenna that recoils upon deflation of the inflatable member.

5. A system for imaging a portion of a human body, the system comprising:
an intravascular device for intravascular manipulation, including an elongate member having a distal end and a proximal end with an inflatable member disposed at the distal end and an antenna coupled to the inflatable member;
the antenna comprising connection pads and one or more conductors, the connection pads coupled to the one or more conductors to form a transmission line in an impedance matching circuit, the antenna coupled to the inflatable member, where inflation of the inflatable member changes a dimension of the antenna and a capacitance in the impedance matching circuit;
a tie layer disposed at an interface between the inflatable member and the antenna, where the tie layer exhibits flexible and elastic characteristics that minimize sheer stress at the interface between the inflatable member and the antenna; and
a magnetic resonance imager coupled to the intravascular device.

6. The system of claim 5, wherein the tie layer comprises at least one of polyvinyl, acetate, nylon or polyester.

7. The system of claim 5, wherein the antenna comprises a fractal antenna.

8. The system of claim 7, wherein the fractal antenna comprises a random fractal antenna.

9. The system of claim 7, wherein the fractal antenna comprises a deterministic fractal antenna.

10. The system of claim 5, wherein the elongate member comprises a catheter.

11. The system of claim 5, wherein the elongate member comprises a guidewire.

12. The system of claim 5, wherein inflation of the inflatable member increases a diameter of the overall conformation of the antenna.

* * * * *

UNITED STATES PATENT AND TRADEMARK OFFICE
CERTIFICATE OF CORRECTION

| | | |
|---|---|---|
| PATENT NO. | : 8,116,846 B2 | Page 1 of 1 |
| APPLICATION NO. | : 12/181948 | |
| DATED | : February 14, 2012 | |
| INVENTOR(S) | : Scott R. Smith | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 365 days.

Signed and Sealed this

Thirtieth Day of October, 2012

David J. Kappos
*Director of the United States Patent and Trademark Office*